(12) United States Patent
Fulmer et al.

(10) Patent No.: US 10,814,112 B2
(45) Date of Patent: *Oct. 27, 2020

(54) DRUG-IMPREGNATED ENCASEMENT

(71) Applicant: DePuy Synthes Products, Inc., Raynham, MA (US)

(72) Inventors: Mark Thomas Fulmer, Glenmoore, PA (US); David A. Armbruster, West Chester, PA (US); Robert Frigg, Bettlach (CH); Elliott A. Gruskin, Malvern, PA (US); Sean Hamilton Kerr, Oreland, PA (US)

(73) Assignee: DePuy Synthes Products, Inc., Raynham, MA (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/726,634

(22) Filed: Oct. 6, 2017

(65) Prior Publication Data

US 2018/0085564 A1    Mar. 29, 2018

Related U.S. Application Data

(63) Continuation of application No. 15/417,409, filed on Jan. 27, 2017, now abandoned, which is a
(Continued)

(51) Int. Cl.
*A61M 31/00* (2006.01)
*A61F 2/06* (2013.01)
(Continued)

(52) U.S. Cl.
CPC .......... *A61M 31/002* (2013.01); *A61B 17/68* (2013.01); *A61B 17/70* (2013.01); *A61B 17/72* (2013.01);
(Continued)

(58) Field of Classification Search
None
See application file for complete search history.

(56) References Cited

U.S. PATENT DOCUMENTS

| 3,155,095 A | 11/1964 | Brown |
| 3,719,736 A | 3/1973 | Woodrupp |

(Continued)

FOREIGN PATENT DOCUMENTS

| AU | 2004202878 A1 | 7/2004 |
| CN | 1206353 A | 1/1999 |

(Continued)

OTHER PUBLICATIONS

Louis et al., Resorbable Mesh as a Containment System in Reconstruction of the Atrophic Mandible Fracture, J Oral Maxillofac Surg, 62, pp. 719-723, Jun. 2004. (Year: 2004).*

(Continued)

*Primary Examiner* — Carlos A Azpuru
*Assistant Examiner* — Casey S Hagopian
(74) *Attorney, Agent, or Firm* — BakerHostetler

(57) ABSTRACT

A drug-impregnated sleeve for encasing a medical implant is provided. In one embodiment, the sleeve may include a body made of a biologically-compatible material that defines an internal cavity configured to receive the medical implant. In one embodiment, the biologically-compatible material is bioresorbable. The body may include a plurality of apertures, such as perforations or holes, extending from the cavity through the body. The sleeve may further include a first end, a second end, and a drug impregnated into the resorbable sheet. In one possible embodiment, the first end of the sleeve may be open for receiving the medical implant therethrough and the second end may be closed. The implant may be encased in the sleeve and implanted into a patient from which the drug is dispensed in vivo over time to tissue (Continued)

surrounding the implantation site. In one embodiment, the body is made from at least one sheet of a biologically-compatible material.

13 Claims, 4 Drawing Sheets

Related U.S. Application Data continuation of application No. 14/503,594, filed on Oct. 1, 2014, now Pat. No. 9,579,260, which is a continuation of application No. 12/089,574, filed as application No. PCT/US2006/040038 on Oct. 12, 2006, now Pat. No. 8,900,620.

(60) Provisional application No. 60/726,808, filed on Oct. 13, 2005.

(51) Int. Cl.
| | | |
|---|---|---|
| A61F 2/07 | (2013.01) | |
| A61B 17/80 | (2006.01) | |
| A61B 17/68 | (2006.01) | |
| A61B 17/70 | (2006.01) | |
| A61B 17/72 | (2006.01) | |
| A61J 3/00 | (2006.01) | |
| A61M 37/00 | (2006.01) | |
| A61L 27/54 | (2006.01) | |
| A61C 8/00 | (2006.01) | |
| A61F 2/04 | (2013.01) | |
| A61L 31/14 | (2006.01) | |
| A61L 31/16 | (2006.01) | |
| A61F 2/30 | (2006.01) | |
| A61B 17/00 | (2006.01) | |

(52) U.S. Cl.
CPC ........ *A61B 17/8028* (2013.01); *A61C 8/0013* (2013.01); *A61F 2/04* (2013.01); *A61F 2/06* (2013.01); *A61F 2/07* (2013.01); *A61J 3/00* (2013.01); *A61L 27/54* (2013.01); *A61L 31/148* (2013.01); *A61L 31/16* (2013.01); *A61M 37/00* (2013.01); *A61B 2017/00004* (2013.01); *A61B 2017/00893* (2013.01); *A61F 2002/072* (2013.01); *A61F 2002/30919* (2013.01); *A61F 2210/0004* (2013.01); *A61F 2250/0067* (2013.01); *A61J 2200/00* (2013.01); *A61M 2205/04* (2013.01); *Y10T 156/1051* (2015.01)

(56) References Cited

U.S. PATENT DOCUMENTS

| | | |
|---|---|---|
| 3,949,037 A | 4/1976 | Volent |
| 4,148,871 A | 4/1979 | Pitt et al. |
| 4,297,993 A | 11/1981 | Harle |
| 4,587,268 A | 5/1986 | Pfirrmann |
| 4,605,414 A | 8/1986 | Czajka |
| 4,605,730 A | 8/1986 | Shalaby et al. |
| 4,659,700 A | 4/1987 | Jackson |
| 4,730,726 A | 3/1988 | Holzwarth |
| 4,774,091 A | 9/1988 | Yamahira et al. |
| 4,863,444 A | 9/1989 | Bloemer |
| 4,888,023 A | 12/1989 | Averill et al. |
| 5,021,241 A | 6/1991 | Yamahira et al. |
| 5,084,050 A | 1/1992 | Draenert |
| 5,093,319 A | 3/1992 | Higham et al. |
| 5,100,668 A | 3/1992 | Edelman et al. |
| 5,104,266 A | 4/1992 | Daryoush et al. |
| 5,147,400 A | 9/1992 | Kaplan et al. |
| 5,260,066 A | 11/1993 | Wood et al. |
| 5,268,178 A | 12/1993 | Calhoun et al. |
| 5,281,221 A | 1/1994 | Tadych |
| 5,324,519 A | 6/1994 | Dunn et al. |
| 5,326,356 A | 7/1994 | Della Valle et al. |
| 5,383,928 A | 1/1995 | Scott et al. |
| 5,456,721 A | 10/1995 | Legrand |
| 5,458,653 A | 10/1995 | Davidson |
| 5,462,563 A | 10/1995 | Shearer et al. |
| 5,468,253 A | 11/1995 | Bezwada et al. |
| 5,489,305 A | 2/1996 | Morgan |
| 5,507,814 A | 4/1996 | Gilbert et al. |
| 5,521,193 A | 5/1996 | Flynn et al. |
| 5,549,676 A | 8/1996 | Johnson |
| 5,567,431 A | 10/1996 | Vert et al. |
| 5,571,204 A | 11/1996 | Nies |
| 5,637,113 A | 6/1997 | Tartaglia et al. |
| 5,656,605 A | 8/1997 | Hansson et al. |
| 5,679,299 A | 10/1997 | Gilbert et al. |
| 5,693,085 A | 12/1997 | Buirge et al. |
| 5,713,904 A | 2/1998 | Errico et al. |
| 5,716,981 A | 2/1998 | Hunter et al. |
| 5,725,570 A | 3/1998 | Heath |
| 5,755,720 A | 5/1998 | Mikhail |
| 5,795,584 A | 8/1998 | Totakura et al. |
| 5,798,113 A | 8/1998 | Dionne et al. |
| 5,800,519 A | 9/1998 | Sandock |
| 5,800,544 A | 9/1998 | Demopulos et al. |
| 5,800,828 A | 9/1998 | Dionne et al. |
| 5,800,829 A | 9/1998 | Dionne et al. |
| 5,824,088 A | 10/1998 | Kirsch |
| 5,834,001 A | 11/1998 | Dionne et al. |
| 5,855,906 A | 1/1999 | McClay |
| 5,869,077 A | 2/1999 | Dionne et al. |
| 5,871,767 A | 2/1999 | Dionne et al. |
| 5,873,906 A | 2/1999 | Lau et al. |
| 5,874,099 A | 2/1999 | Dionne et al. |
| 5,876,432 A | 3/1999 | Lau et al. |
| 5,919,225 A | 7/1999 | Lau et al. |
| 5,919,235 A | 7/1999 | Husson et al. |
| 5,947,893 A | 9/1999 | Agrawal et al. |
| 5,955,095 A | 9/1999 | Gentile et al. |
| 5,984,926 A | 11/1999 | Jones |
| 6,001,123 A | 12/1999 | Lau |
| 6,013,104 A | 1/2000 | Kampner |
| 6,015,429 A | 1/2000 | Lau et al. |
| 6,017,362 A | 1/2000 | Lau |
| 6,060,640 A | 5/2000 | Pauley et al. |
| 6,063,395 A | 5/2000 | Markkula et al. |
| 6,071,567 A | 6/2000 | Castelli et al. |
| 6,083,523 A | 7/2000 | Dionne et al. |
| 6,117,442 A | 9/2000 | Markkula et al. |
| 6,143,029 A | 11/2000 | Rippstein |
| 6,143,033 A | 11/2000 | Paul et al. |
| 6,165,202 A | 12/2000 | Kokish et al. |
| 6,165,210 A | 12/2000 | Lau et al. |
| 6,180,052 B1 | 1/2001 | Ouellette et al. |
| 6,193,746 B1 | 2/2001 | Strecker |
| 6,221,097 B1 | 4/2001 | Wang et al. |
| 6,232,869 B1 | 5/2001 | Choi |
| 6,235,869 B1 | 5/2001 | Roby et al. |
| 6,248,112 B1 | 6/2001 | Gambale et al. |
| 6,254,627 B1 | 7/2001 | Freidberg |
| 6,258,125 B1 | 7/2001 | Paul et al. |
| 6,277,084 B1 | 8/2001 | Abele et al. |
| 6,280,411 B1 | 8/2001 | Lennox |
| 6,287,291 B1 | 9/2001 | Bigus et al. |
| 6,287,331 B1 | 9/2001 | Heath |
| 6,287,628 B1 | 9/2001 | Hossainy et al. |
| 6,287,638 B1 | 9/2001 | Castelli et al. |
| 6,290,721 B1 | 9/2001 | Heath |
| 6,299,894 B1 | 10/2001 | Markkula et al. |
| 6,306,166 B1 | 10/2001 | Barry et al. |
| 6,322,804 B1 | 11/2001 | Dionne et al. |
| 6,331,186 B1 | 12/2001 | Wang et al. |
| 6,331,188 B1 | 12/2001 | Lau et al. |
| 6,337,088 B1 | 1/2002 | Gentile et al. |
| 6,350,284 B1 | 2/2002 | Tormala et al. |
| 6,379,381 B1 | 4/2002 | Hossainy et al. |
| 6,383,190 B1 | 5/2002 | Preissman |

(56) References Cited

U.S. PATENT DOCUMENTS

| | | |
|---|---|---|
| 6,419,694 B1 | 7/2002 | Sandock |
| 6,432,141 B1 | 8/2002 | Stocks et al. |
| 6,443,980 B1 | 9/2002 | Wang et al. |
| 6,447,522 B2 | 9/2002 | Gambale et al. |
| 6,451,003 B1 | 9/2002 | Prosl et al. |
| 6,451,050 B1 | 9/2002 | Rudakov et al. |
| 6,468,300 B1 | 10/2002 | Freidberg |
| 6,476,079 B1 | 11/2002 | Jukarainen et al. |
| 6,482,235 B1 | 11/2002 | Lambrecht et al. |
| 6,491,720 B1 | 12/2002 | Vallana et al. |
| 6,494,898 B1 | 12/2002 | Roby et al. |
| 6,497,709 B1 | 12/2002 | Heath |
| 6,503,556 B2 | 1/2003 | Harish et al. |
| 6,503,954 B1 | 1/2003 | Bhat et al. |
| 6,517,570 B1 | 2/2003 | Lau et al. |
| 6,520,984 B1 | 2/2003 | Garrison et al. |
| 6,545,097 B2 | 4/2003 | Pinchuk et al. |
| 6,547,812 B1 | 4/2003 | Hu |
| 6,554,863 B2 | 4/2003 | Paul et al. |
| 6,569,180 B1 | 5/2003 | Sirhan et al. |
| 6,592,569 B2 | 7/2003 | Bigus et al. |
| 6,592,885 B2 | 7/2003 | Phaneuf et al. |
| 6,596,296 B1 | 7/2003 | Nelson et al. |
| 6,602,290 B2 | 8/2003 | Esnouf et al. |
| 6,607,544 B1 | 8/2003 | Boucher et al. |
| 6,613,072 B2 | 9/2003 | Lau et al. |
| 6,632,235 B2 | 10/2003 | Weikel et al. |
| 6,641,587 B2 | 11/2003 | Scribner et al. |
| 6,645,241 B1 | 11/2003 | Strecker |
| 6,660,038 B2 | 12/2003 | Boyer, II et al. |
| 6,666,880 B1 | 12/2003 | Chiu et al. |
| 6,692,498 B1 | 2/2004 | Niiranen et al. |
| 6,706,058 B2 | 3/2004 | Hierlemann et al. |
| 6,713,119 B2 | 3/2004 | Hossainy et al. |
| 6,716,216 B1 | 4/2004 | Boucher et al. |
| 6,716,444 B1 | 4/2004 | Castro et al. |
| 6,719,773 B1 | 4/2004 | Boucher et al. |
| 6,726,691 B2 | 4/2004 | Osorio et al. |
| 6,746,483 B1 | 6/2004 | Bojarski et al. |
| 6,749,626 B1 | 6/2004 | Bhat et al. |
| 6,759,054 B2 | 7/2004 | Chen et al. |
| 6,767,369 B2 | 7/2004 | Boyer, II et al. |
| 6,790,224 B2 | 9/2004 | Gerberding |
| 6,790,228 B2 | 9/2004 | Hossainy et al. |
| RE38,614 E | 10/2004 | Synthes |
| 6,818,247 B1 | 11/2004 | Chen et al. |
| 6,827,743 B2 | 12/2004 | Eisermann et al. |
| 6,840,770 B2 | 1/2005 | McDevitt |
| 6,855,770 B2 | 2/2005 | Pinchuk et al. |
| 6,863,530 B2 | 3/2005 | McDevitt |
| 6,863,692 B2 | 3/2005 | Meulink |
| 6,883,520 B2 | 4/2005 | Lambrecht et al. |
| 6,884,427 B1 | 4/2005 | Barrows |
| 6,899,719 B2 | 5/2005 | Reiley et al. |
| 6,908,624 B2 | 6/2005 | Hossainy et al. |
| 6,946,143 B2 | 9/2005 | Kim et al. |
| 6,953,560 B1 | 10/2005 | Castro et al. |
| 6,960,351 B2 | 11/2005 | Dionne et al. |
| 6,979,341 B2 | 12/2005 | Scribner et al. |
| 6,981,991 B2 | 1/2006 | Ferree |
| 6,986,788 B2 | 1/2006 | Paul et al. |
| 7,001,390 B2 | 2/2006 | Gebhardt et al. |
| 7,014,659 B2 | 3/2006 | Boyer, II et al. |
| 7,025,791 B2 | 4/2006 | Levine et al. |
| 7,037,332 B2 | 5/2006 | Kutryk et al. |
| 7,041,308 B2 | 5/2006 | Shalaby et al. |
| 7,056,577 B1 | 6/2006 | Bruce et al. |
| 7,070,613 B2 | 7/2006 | Weber et al. |
| 7,087,082 B2 | 8/2006 | Paul et al. |
| 7,087,087 B2 | 8/2006 | Boyer et al. |
| 7,101,392 B2 | 9/2006 | Heath |
| 7,108,717 B2 | 9/2006 | Freidberg |
| 7,115,146 B2 | 10/2006 | Boyer et al. |
| 7,122,058 B2 | 10/2006 | Levine et al. |
| 7,131,986 B2 | 11/2006 | Sirhan et al. |
| 7,137,993 B2 | 11/2006 | Acosta et al. |
| 7,147,656 B2 | 12/2006 | Andreas et al. |
| 7,153,306 B2 | 12/2006 | Ralph et al. |
| 7,153,307 B2 | 12/2006 | Scribner et al. |
| 7,168,605 B2 | 1/2007 | Walak |
| 7,169,405 B2 | 1/2007 | Trieu |
| 7,175,873 B1 | 2/2007 | Roorda et al. |
| 7,182,779 B2 | 2/2007 | Acosta et al. |
| 7,192,448 B2 | 3/2007 | Ferree |
| 7,198,047 B2 | 4/2007 | Lambrecht et al. |
| 7,208,008 B2 | 4/2007 | Clarke |
| 7,238,168 B2 | 7/2007 | Sirhan et al. |
| 7,247,313 B2 | 7/2007 | Roorda et al. |
| 7,252,671 B2 | 8/2007 | Scribner et al. |
| 7,261,720 B2 | 8/2007 | Stevens et al. |
| 7,267,694 B2 | 9/2007 | Levine et al. |
| 7,270,668 B2 | 9/2007 | Andreas et al. |
| 7,279,008 B2 | 10/2007 | Brown et al. |
| 7,279,175 B2 | 10/2007 | Chen et al. |
| 7,294,146 B2 | 11/2007 | Chew et al. |
| 7,296,998 B2 | 11/2007 | Bartee et al. |
| 7,300,456 B2 | 11/2007 | Andreas et al. |
| 7,300,465 B2 | 11/2007 | Paul et al. |
| 7,309,350 B2 | 12/2007 | Landreville et al. |
| 7,311,727 B2 | 12/2007 | Mazumder et al. |
| 7,329,285 B2 | 2/2008 | Levine et al. |
| 7,347,873 B2 | 3/2008 | Paul et al. |
| 7,347,875 B2 | 3/2008 | Levine et al. |
| 7,351,255 B2 | 4/2008 | Andreas |
| 7,357,812 B2 | 4/2008 | Andreas et al. |
| 7,402,172 B2 | 7/2008 | Chin et al. |
| 7,407,512 B2 | 8/2008 | Bojarski et al. |
| 7,458,990 B2 | 12/2008 | Chieng |
| 7,465,318 B2 | 12/2008 | Sennett et al. |
| 7,473,277 B2 | 1/2009 | Boyer, II et al. |
| 7,491,234 B2 | 2/2009 | Palasis et al. |
| 7,503,936 B2 | 3/2009 | Trieu |
| 7,504,125 B1 | 3/2009 | Pacetti et al. |
| 7,550,012 B2 | 6/2009 | Lavelle |
| 7,553,539 B2 | 6/2009 | Bruce et al. |
| 7,578,834 B2 | 8/2009 | Abdou |
| 7,608,114 B2 | 10/2009 | Levine et al. |
| 7,611,481 B2 | 11/2009 | Cleary et al. |
| 7,618,432 B2 | 11/2009 | Pedersen et al. |
| 7,618,448 B2 | 11/2009 | Schmitz et al. |
| 7,618,647 B2 | 11/2009 | Weber et al. |
| 7,622,146 B2 | 11/2009 | Roorda et al. |
| 7,622,530 B2 | 11/2009 | Pinchuk et al. |
| 7,666,216 B2 | 2/2010 | Hogendijk et al. |
| 7,678,068 B2 | 3/2010 | Levine et al. |
| 7,682,647 B2 | 3/2010 | Hossainy et al. |
| 7,686,781 B2 | 3/2010 | Vinten-Johansen |
| 7,691,401 B2 | 4/2010 | Castro et al. |
| 7,695,446 B2 | 4/2010 | Levine et al. |
| 7,698,111 B2 | 4/2010 | Abrahao et al. |
| 7,704,545 B2 | 4/2010 | Kantor |
| 7,731,750 B2 | 6/2010 | Bojarski et al. |
| 7,740,657 B2 | 6/2010 | Brown et al. |
| 7,744,620 B2 | 6/2010 | Pedersen et al. |
| 7,758,535 B2 | 7/2010 | Levine et al. |
| 7,758,642 B2 | 7/2010 | Bojarski et al. |
| 7,758,881 B2 | 7/2010 | Dugan |
| 7,766,861 B2 | 8/2010 | Levine et al. |
| 7,766,973 B2 | 8/2010 | Levine et al. |
| 7,771,382 B2 | 8/2010 | Levine et al. |
| 7,785,615 B2 | 8/2010 | Dave et al. |
| 7,789,915 B2 | 9/2010 | Lavelle et al. |
| 7,803,183 B2 | 9/2010 | Kutryk et al. |
| 7,988,732 B2 | 8/2011 | Bojarski et al. |
| 8,900,620 B2 * | 12/2014 | Fulmer ............ A61F 2/06 424/426 |
| 9,381,683 B2 | 7/2016 | Armbruster et al. |
| 9,579,260 B2 * | 2/2017 | Fulmer ............ A61F 2/06 |
| 2001/0039456 A1 | 11/2001 | Boyer et al. |
| 2002/0055749 A1 | 5/2002 | Esnouf et al. |
| 2002/0062147 A1 | 5/2002 | Yang |
| 2002/0187260 A1 | 12/2002 | Sheppard et al. |
| 2003/0088307 A1 | 5/2003 | Shulze et al. |

(56) References Cited

U.S. PATENT DOCUMENTS

| | | | |
|---|---|---|---|
| 2003/0093111 A1* | 5/2003 | Ken | A61B 17/12145 606/200 |
| 2003/0107149 A1 | 6/2003 | Yang et al. | |
| 2003/0149466 A1 | 8/2003 | Gerberding | |
| 2004/0093058 A1 | 5/2004 | Cottone et al. | |
| 2004/0093062 A1 | 5/2004 | Glastra | |
| 2004/0146546 A1 | 7/2004 | Gravett et al. | |
| 2004/0225359 A1 | 11/2004 | Bojarski et al. | |
| 2004/0267347 A1 | 12/2004 | Cervantes | |
| 2004/0267354 A1 | 12/2004 | Ringeisen et al. | |
| 2005/0019404 A1 | 1/2005 | Sung et al. | |
| 2005/0129732 A1 | 6/2005 | Rubsamen | |
| 2005/0159805 A1 | 7/2005 | Weber et al. | |
| 2005/0181977 A1 | 8/2005 | Hunter et al. | |
| 2005/0209629 A1 | 9/2005 | Kerr et al. | |
| 2005/0209704 A1 | 9/2005 | Maspero et al. | |
| 2005/0246021 A1* | 11/2005 | Ringeisen | A61B 17/846 623/17.11 |
| 2005/0261782 A1 | 11/2005 | Hoganson | |
| 2005/0278011 A1 | 12/2005 | Peckham | |
| 2006/0093646 A1 | 5/2006 | Cima et al. | |
| 2006/0234061 A1 | 10/2006 | Buckel et al. | |
| 2006/0259122 A1 | 11/2006 | Eliseev | |
| 2006/0263355 A1 | 11/2006 | Quan et al. | |
| 2006/0276906 A1 | 12/2006 | Hoag et al. | |
| 2006/0286137 A1 | 12/2006 | Sandhu et al. | |
| 2007/0038299 A1 | 2/2007 | Stone et al. | |
| 2007/0118211 A1 | 5/2007 | Gazza | |
| 2007/0141103 A1 | 6/2007 | Benedict et al. | |
| 2007/0142892 A1 | 6/2007 | Dave et al. | |
| 2007/0198040 A1 | 8/2007 | Buevich et al. | |
| 2007/0213801 A1 | 9/2007 | Kutryk et al. | |
| 2007/0255422 A1 | 11/2007 | Wei et al. | |
| 2008/0033548 A1 | 2/2008 | Xuenong et al. | |
| 2008/0057096 A1 | 3/2008 | Ibsen et al. | |
| 2008/0097570 A1 | 4/2008 | Thornton et al. | |
| 2008/0107711 A1 | 5/2008 | Shelokov | |
| 2008/0112892 A1 | 5/2008 | Veenstra et al. | |
| 2008/0125847 A1 | 5/2008 | Krever et al. | |
| 2008/0128315 A1 | 6/2008 | Buevich et al. | |
| 2008/0132922 A1 | 6/2008 | Buevich et al. | |
| 2008/0132992 A1 | 6/2008 | Bates et al. | |
| 2008/0195218 A1 | 8/2008 | Jones | |
| 2008/0241212 A1 | 10/2008 | Moses et al. | |
| 2008/0262630 A1 | 10/2008 | Fulmer et al. | |
| 2009/0012595 A1 | 1/2009 | Seliktar et al. | |
| 2009/0018640 A1 | 1/2009 | State | |
| 2009/0062899 A1 | 3/2009 | Dang et al. | |
| 2009/0069904 A1 | 3/2009 | Picha | |
| 2009/0076449 A1 | 3/2009 | Geis et al. | |
| 2009/0076508 A1 | 3/2009 | Weinans et al. | |
| 2009/0081276 A1 | 3/2009 | Alsberg et al. | |
| 2009/0081278 A1 | 3/2009 | De Graaff et al. | |
| 2009/0092654 A1 | 4/2009 | de Juan, Jr. et al. | |
| 2009/0118817 A1 | 5/2009 | Sandhu et al. | |
| 2009/0130167 A1 | 5/2009 | Shelton et al. | |
| 2009/0143851 A1 | 6/2009 | Paul, Jr. | |
| 2009/0192474 A1 | 7/2009 | Wei et al. | |
| 2009/0192609 A1 | 7/2009 | Klabunde et al. | |
| 2009/0198197 A1 | 8/2009 | Bischoff et al. | |
| 2009/0227948 A1 | 9/2009 | Chen et al. | |
| 2009/0233045 A1 | 9/2009 | Slama et al. | |
| 2009/0234453 A1 | 9/2009 | Steinberg | |
| 2009/0289395 A1 | 11/2009 | Chou | |
| 2010/0004729 A1 | 1/2010 | Chew et al. | |
| 2010/0028390 A1 | 2/2010 | Cleary et al. | |
| 2010/0028402 A1 | 2/2010 | Dobrovolskaia et al. | |
| 2010/0070015 A1 | 3/2010 | Schneider et al. | |
| 2010/0211153 A1 | 8/2010 | Cook et al. | |
| 2010/0222826 A1 | 9/2010 | Bojarski et al. | |
| 2010/0228333 A1 | 9/2010 | Drasler et al. | |
| 2010/0233238 A1 | 9/2010 | Tenney et al. | |
| 2010/0241214 A1 | 9/2010 | Shaked et al. | |
| 2010/0247600 A1 | 9/2010 | Xia et al. | |
| 2010/0249783 A1 | 9/2010 | Trieu | |
| 2011/0144688 A1 | 6/2011 | Reiss et al. | |
| 2011/0244047 A1 | 10/2011 | Asari et al. | |
| 2011/0268781 A1 | 11/2011 | Cleek et al. | |
| 2011/0282362 A1 | 11/2011 | Bojarski et al. | |
| 2012/0010636 A1 | 1/2012 | Boey et al. | |
| 2012/0016388 A1 | 1/2012 | Houard et al. | |
| 2012/0027833 A1 | 2/2012 | Zilberman | |
| 2013/0129807 A1 | 5/2013 | Devore et al. | |
| 2013/0289621 A1 | 10/2013 | Agarwal et al. | |

FOREIGN PATENT DOCUMENTS

| | | |
|---|---|---|
| CN | 1638743 | 7/2005 |
| CN | 101402736 A | 4/2009 |
| CN | 101437571 | 5/2009 |
| CN | 101912663 A | 12/2010 |
| CN | 102958557 A | 3/2013 |
| DE | 3939363 A1 | 6/1991 |
| EP | 0013638 A1 | 7/1980 |
| EP | 0323800 A1 | 7/1989 |
| EP | 0371819 A2 | 6/1990 |
| EP | 0523926 A2 | 1/1993 |
| EP | 0539751 A1 | 5/1993 |
| EP | 0578998 A1 | 1/1994 |
| EP | 0604697 A1 | 7/1994 |
| EP | 0737703 A2 | 10/1996 |
| EP | 1216717 A1 | 6/2002 |
| EP | 1272131 A2 | 1/2003 |
| EP | 1294323 A2 | 3/2003 |
| EP | 1374817 A1 | 1/2004 |
| EP | 1395303 A2 | 3/2004 |
| EP | 1482996 B1 | 11/2005 |
| EP | 1812090 A1 | 8/2007 |
| EP | 1820463 A2 | 8/2007 |
| EP | 1463463 B1 | 2/2008 |
| EP | 1913903 A2 | 4/2008 |
| EP | 2052700 A1 | 4/2009 |
| EP | 2080603 A1 | 7/2009 |
| FR | 1181333 A | 6/1959 |
| FR | 1183333 A | 7/1959 |
| JP | 02-121652 | 5/1990 |
| JP | 03-085179 A | 4/1991 |
| JP | 04-221538 | 8/1992 |
| JP | 07-044936 B2 | 5/1995 |
| JP | 07-313586 | 12/1995 |
| JP | 08-024347 | 1/1996 |
| JP | 08-224297 | 9/1996 |
| JP | 09-173364 A | 7/1997 |
| JP | 09-201330 | 8/1997 |
| JP | 2002-058741 A | 2/2002 |
| JP | 2003-527193 A | 9/2003 |
| JP | 2008-531699 | 8/2008 |
| JP | 2008-224297 A | 9/2008 |
| JP | 2008-535700 A | 9/2008 |
| JP | 2009-511196 A | 3/2009 |
| JP | 2009-240783 A | 10/2009 |
| JP | 2011-216178 A | 10/2011 |
| JP | 2013-005984 A | 1/2013 |
| RU | 2234419 C2 | 8/2004 |
| RU | 2300792 C2 | 6/2007 |
| RU | 77539 U1 | 10/2008 |
| SU | 683207 A1 | 3/1985 |
| WO | 98/51240 A1 | 11/1998 |
| WO | 99/51171 A1 | 10/1999 |
| WO | 99/62416 A1 | 12/1999 |
| WO | 00/12147 A1 | 3/2000 |
| WO | 01/12107 A1 | 2/2001 |
| WO | 01/32100 A2 | 5/2001 |
| WO | 01/70135 A2 | 9/2001 |
| WO | 01/76514 A2 | 10/2001 |
| WO | 01/97721 A2 | 12/2001 |
| WO | 02/51463 A2 | 7/2002 |
| WO | 03/22165 A1 | 3/2003 |
| WO | 03/59213 A2 | 7/2003 |
| WO | 2004/010854 A2 | 2/2004 |
| WO | 2005/009499 A1 | 2/2005 |
| WO | 2005/049105 A2 | 6/2005 |
| WO | 2006/023261 A2 | 3/2006 |
| WO | 2006/050106 A1 | 5/2006 |

(56) References Cited

FOREIGN PATENT DOCUMENTS

| WO | 2006/108520 | A1 | 10/2006 |
|---|---|---|---|
| WO | 2007/047420 | A2 | 4/2007 |
| WO | 2007/053022 | A2 | 5/2007 |
| WO | 2007/092417 | A1 | 8/2007 |
| WO | 2008/121816 | A2 | 10/2008 |
| WO | 2010/135440 | A1 | 11/2010 |
| WO | 2013/013172 | A1 | 1/2013 |

OTHER PUBLICATIONS

Definition of "textile" accessed online at https://www.merriam-webster.com on Jun. 16, 2020. (Year: 2020).*
Zhang et al., Biodegradable Controlled Antibiotic Release Devices for Osteomyelitis: Optimization of Release Properties, Journal of Pharmacy and Pharmacology, Sep. 1994, vol. 46, Issue 9.
Written Opinion of the International Searching Authority for Application No. PCT/US2006/40038, dated Sep. 25, 2007, 6 pages.
Von Plocki et al., "Biodegradable Sleeves for Metal Implants to Prevent Implant-Associated Infection: An Experimental In Vivo Study in Sheep", Vet Surg., Apr. 2012, 41(3), 410-421, Epub Jan. 12, 2012.
U.S. Application Filed on Oct. 13, 2005 by Kerr et al., U.S. Appl. No. 60/726,808.
Trampuz et al., "Diagnosis and Treatment of Infections Associated with Fracture-Fixation Devices", Injury, May 2006, 37, Suppl 2, S59-S66.
Stile et al., "Synthesis and Characterization of Injectable Poly(N-isopropylacrylamide)-Based Hydrogels That Support Tissue Formation in Vitro", Macromolecules, 32, (1999), 7370-7379.
Second Office Action for Chinese Patent Application No. 200680037881.8 dated Dec. 23, 2011.
Schmidt et al., Antibiotic in vivo/in vitro release, histocompatibility and biodegradation of gentamicin implants based on lactic acid polymers and copolymers, Nov. 1995, Journal of Controlled Release, vol. 37, Issues 1-2, pp. 83-84.
Pineros-Fernandez, A. et al., "CAPROSYN*, Another Major Advance in Synthetic Monofilament Absorbable Suture", Journal of Long-Term Effects of Medical Implants, 2004, 14(5), 359-368.
Pandey et al., Characterization of In-vitro Release of Gentamicin from Biodegradable Polymer Thin Films Microstructure—Function Relationship by Confocal Raman Microscopy, Apr. 2015, Journal of Biomedical Materials Research.
Office action dated Oct. 18, 2011 for Japanese Patent Application No. 2008-535700.
Mingeot-Leclercq et al., "Aminoglycosides: Nephrotoxicity", Antimicrobial Agents and Chemotherapy, May 1999, 43 (5), 1003-1012.
Machine Translation of DE 3939363 A1, Jun. 1991, 9 pages.
Lucke, M, et al., "Gentamicin coating of metallic implants reduces implant-related osteomyelitis in rats", Bone; vol. 32, (2003), 521-531.
Kaneko, Y., et al., "Synthesis and Swelling—deswelling kinetics of poly(N-isopropylacrylamide) hydrogels grafted with LCST modulated polymers", Journal of Biomaterials Science Polymer Edition 10(11) (1999),1079-1091.
Japanese Application No. 2002-506661, Official Notice of Reason for the Final Rejection dated Jul. 11, 2008, (w/ English Translation), 4 pgs.
Japanese Application No. 2002-506661, Notice of the Reason for the Rejection dated Feb. 27, 2008, (w/ English Translation), 7 pgs.
International Patent Application No. PCT/US2012/071708: International Search Report and Written Opinion dated Jun. 5, 2013, 22 pages.
International Application Serial No. PCT/US06/40038, Written Opinion dated Sep. 25, 2007, 6 Pgs.
International Application Serial No. PCT/US06/40038, International Search Reoort dated Sep. 25, 2007, 3 Pgs.
International Application Serial No. PCT/US06/40038, International Preliminary Report on Patentability dated Mar. 2008, 7 Pgs.
Huang et al., On the importance and mechanisms of burst release in matrix-controlled drug delivery systems, Jun. 2001, Journal of Controlled Release, vol. 73, Issues 2-3, pp. 121-136.
Gupta et al., Cefoperazone sodium impregnated polycaprolactone composite implant for osteomyelitis, Indian J. Pharm Sci, Jul.-Aug. 2009, 71(4) 377-381.
Gosau et al., "Release of Gentamicin Sulphate From Biodegradable PLGA-Implants Produced by Hot Melt Extrusion", Pharmazie, 2010.
Fredenberg et al., The mechanisms of drug release in poly(lactic-co-glycolic acid)-based drug delivery systems?A review, Aug. 2011, International Journal of Pharmaceutics, vol. 415, Issues 1-2, pp. 34-52.
Final Office Action for Japanese Patent Application No. 2008-535700 dated May 24, 2012.
European Patent Application No. 04750971.6, Communication dated Jun. 12, 2008, 5 pages.
Dorta et al., Potential applications of PLGA film-implants in modulating in vitro drugs release, Nov. 2002, International Journal of Pharmaceutics, vol. 248, Issues 1-2, pp. 149-156.
Darouiche, R. 0., "Treatment of Infections Associated with Surgical Implants", The New England Journal of Medicine, Apr. 2004, 350(14), 1422-1429.
Bailey, T. C. et al., "A Meta-Analysis of Extended-Interval Dosing Versus Multiple Daily Dosing of Aminoglycosides", Clinical Infectious Diseases, May 1997, 24, 786-795.
Aviv et al., "Gentamicin-Loaded Bioresorbable Films for Prevention of Bacterial Infections Associated with Orthopedic Implants", Journal of Biomedical Materials Research Part 1, Mar. 2007, 10 pages.

* cited by examiner

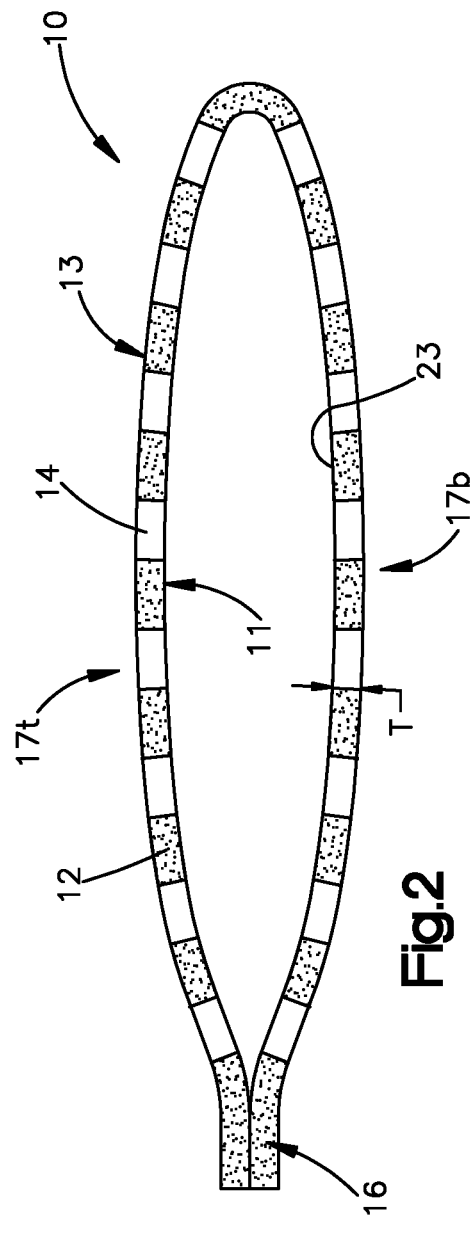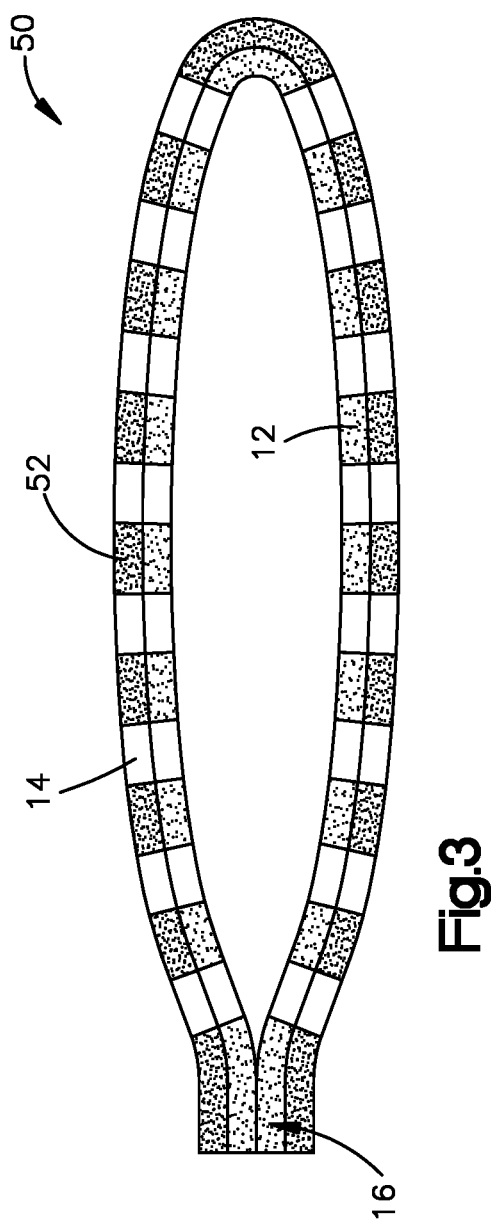

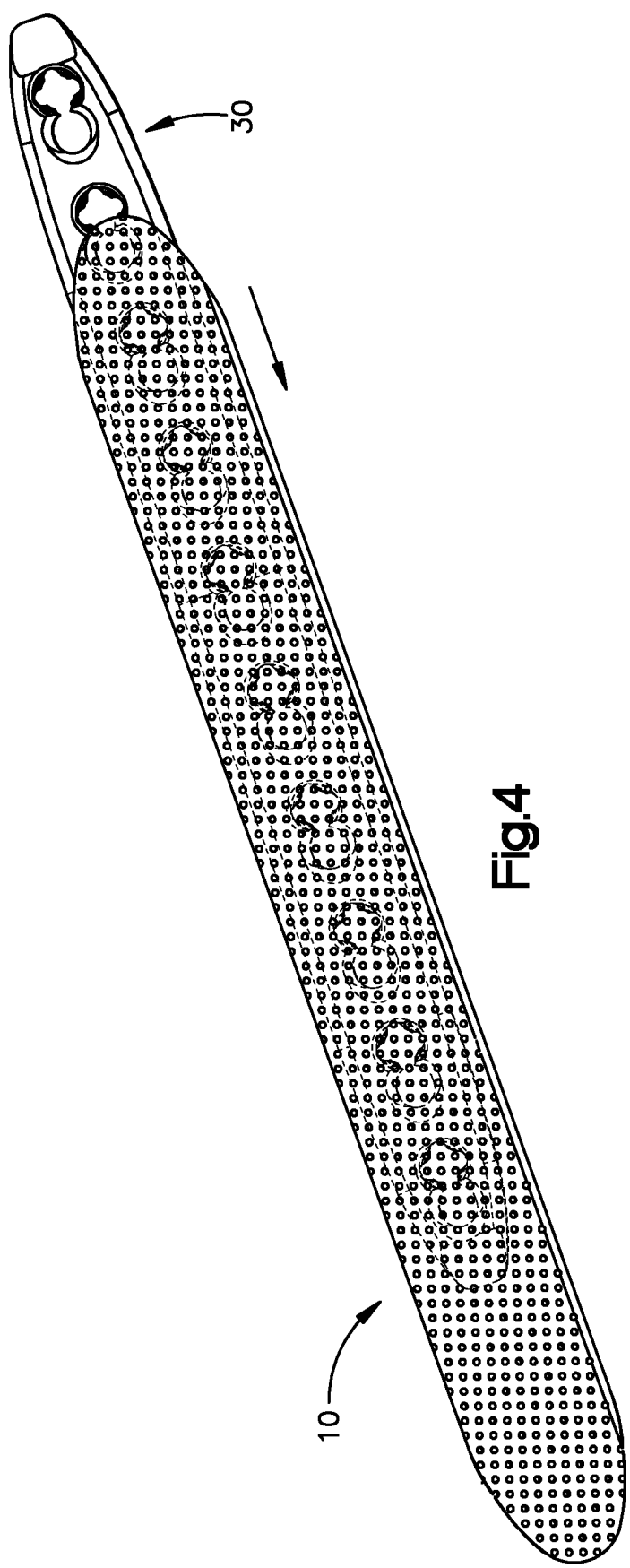
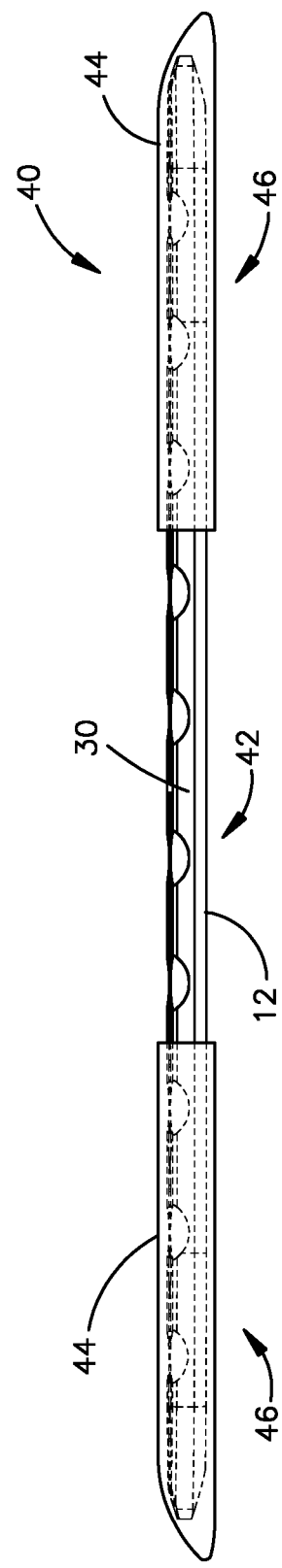
Fig.4
Fig.5

DRUG-IMPREGNATED ENCASEMENT

CROSS-REFERENCE TO RELATED APPLICATION

This application is a continuation of U.S. application Ser. No. 15/417,409, filed Jan. 27, 2017, which is a continuation of U.S. application Ser. No. 14/503,594, filed on Oct. 1, 2014, now U.S. Pat. No. 9,579,260, which is a continuation of U.S. application Ser. No. 12/089,574, filed Apr. 8, 2008, now U.S. Pat. No. 8,900,620, which is national stage 371 application of PCT/US2006/040038, filed Oct. 12, 2006, which claims priority to U.S. Provisional Application Ser. No. 60/726,808, filed Oct. 13, 2005, the disclosures of which are hereby incorporated by reference as if set forth in their entirety herein.

FIELD OF THE INVENTION

The present invention relates to an improved drug-impregnated encasement that is configured and adapted to receive a medical implant, and more particularly to a sleeve in one embodiment that is operative to encase orthopedic implants of varying types, sizes, and shapes for delivering a drug to the implantation site.

BACKGROUND OF THE INVENTION

Colonization of bacteria on the surface of implants often leads to infections. Systemic antibiotics can reduce the risk of infection; however infections can still develop on the surface of implants even in the presence of systemic prophylactic antibiotics. It is not uncommon for orthopedic surgeons to treat implant sites with local antibiotics or other biologically active agents. In some cases the surgeon mixes an antibiotic with PMMA bone cement to prepare a local antibiotic depot. In other cases, to provide a more uniform and easy to use solution, bioresorbable surface coatings or films have been developed that may be applied to orthopedic implants. The coatings may be impregnated with a drug or antibiotic such as gentamicin. Such coatings may be applied to a wide variety of orthopedic implants, such as other tibia or other nails, plates, or screws. In general the coatings are derived from resorbable polymers so that when the drug is depleted, the implant remains while the coating has dissolved away.

One problem with coated implants is that each coated implant represents a new development product in which the coating method, new packaging and sterilization methods must be validated. In addition, each coated implant is the subject of a separate regulatory submission. As a result, a broad portfolio of drug-coated implants is a major undertaking. The logistical challenge is exacerbated by the prospect of using a variety of coatings including materials such as analgesics, antineoplastic agents, bisphosphonates and growth promoting substances.

Given the large number, sizes, and shapes of potential coated products, the regulatory, financial, and logistical burden of providing uncoated and coated implants is enormous. The problem is amplified if one considers additional drugs to use in coatings such as analgesics, antineoplastic agents and growth promoting substances. Moreover, in some of these instances the drug must be deployed into the bone and not the surrounding soft tissue which can constitute the majority of the tissue contacting zones in a typical implant.

SUMMARY OF THE INVENTION

Accordingly, there remains a need for an improved drug-release means that can universally accommodate a wide variety of implants and provide a cost-effective solution to the limitations of conventional surface coatings. The invention is generally directed to an improved drug-impregnated encasement. Preferably, the encasement is made from a biologically-compatible material, which is broadly defined herein as any approved FDA material suitable for implantation in a patient. In a preferred embodiment, the encasement is made from, but is not limited to a bioresorbable material. In one preferred embodiment, the encasement is configured as a sleeve. The present invention provides a "one-size fits all" solution to the foregoing coated-implant problem. Instead of creating an inventory of numerous different coated implants, a drug-impregnated sleeve is alternatively provided that preferably can fit a range of different conventional uncoated implants. According to one aspect of the invention, therefore, the drug-impregnated sleeve is configured to advantageously accommodate a wide variety of implant types, shapes, and sizes.

According to another aspect of the invention, the sleeve is implanted into a patient and the drug is dispensed from the sleeve in vivo over time to tissue surrounding the implantation site. In one embodiment, the duration and dosage of the drug delivered to the patient from the sleeve may be controlled by such factors as the choice of sleeve material used, construction of the sleeve, and type and form of drug or combination of drugs and/or drug delivery systems impregnated into the sleeve as further described herein.

According to another aspect of the invention, the drug-impregnated sleeve may advantageously be modified and adapted by the surgeon to custom fit the sleeve to the particular size and shape of the implant needed to be encased. Also advantageously, in one embodiment the sleeve may be modified by the surgeon in the operating room and then slipped over the implant. This approach is beneficial where the surgeon may not be certain of which type or size of an implant, such as a bone plate for example, is required for a bone fixation procedure until the implant site can be accessed during surgery for visual observation and measurement. The surgeon may then select the proper type and size of the implant, and cut the drug-impregnated sleeve to fit.

One or more illustrative drugs or biological agents that may be impregnated into the sleeve includes without limitation antibiotics, antiseptics, analgesics, antineoplastic agents, bisphosphonates, growth factors, peptides, statins, etc. It will be appreciated that any type of drug or biological agent may be incorporated into the sleeve and the invention is not limited by the type used. It should be noted that any reference herein to a "drug" is broadly defined as any medically-related biological agent that may beneficially be incorporated into the sleeve for dispensing to the implantation site of a medical implant. It should be further noted that the invention may be used with any type of medical implant (defined herein to include dental implants) and is expressly not limited to use with orthopedic implants alone.

A preferred embodiment of a drug-impregnated sleeve for encasing a medical implant generally includes a body made of at least one sheet of a biologically-compatible material, a first end, a second end, and a drug impregnated into the sheet. In one embodiment, the biologically-compatible material is bioresorbable. In one embodiment, the drug is dispensed in vivo from the sleeve to an implantation site in a patient after the medical implant is installed. In one embodiment, the body defines an internal cavity that is configured to receive a medical implant. In one embodiment, the body preferably further includes a plurality of apertures extending from the cavity through the body. In one embodiment, the apertures may be round perforations. In another embodiment, the apertures may have a form selected from the group consisting of round holes, elliptical holes, slits, slots, or any combination thereof. In one embodiment, the medical device may be an orthopedic device, which in some embodiments may be a bone fixation plate or intramedullary nail such as a tibia or femoral nail. Preferably, the first end of the sleeve may be open for receiving the medical implant therethrough and the second end may be closed. In one embodiment, the sleeve may be generally elongate in shape. In another embodiment, the sleeve has a top and bottom, at least a portion of the top or bottom being substantially planar. In another embodiment, the sleeve includes a first edge having a seam closing the first edge and the second end includes a seam closing the second end.

In one embodiment, a resorbable sheet preferably includes a polymer, and more preferably includes caprolactone for adding flexibility and pliability to the sleeve to facilitate sliding the sleeve over the implant and conforming the sleeve to the general shape of the implant. In one embodiment, the sheet may contain different salts of the same drug to control the rate and duration of drug release into the patient. In other embodiments, wherein the sheet may contain two different drugs. In another embodiment, the sleeve is made from at least two sheets of resorbable material that are laminated together. At least one sheet may be microporous in some embodiments. In other embodiments, the at least two sheets may contain different drugs.

Another possible embodiment of a drug-impregnated sleeve for encasing a medical implant generally includes at least one sheet made of a biologically-compatible material and at least one drug impregnated into the sheet. In one embodiment, the biologically-compatible material is bioresorbable. The sheet may contain a plurality of apertures, which in one embodiment may be round perforations or holes. In one embodiment, the sheet may be folded to create a rolled edge, an opposite free edge, a first end, and a second end opposite the first end. In one embodiment, a seam may be formed along the free edge and the second end so that the seam closes the free edge and second end. In one embodiment, the first end defines an opening configured for receiving a medical implant therethrough to be at least partially encased by the sleeve. The sleeve may be sized and configured to conform to the general shape of the types and sizes of medical implants intended to be encased within the sleeve.

A method of forming a drug-impregnated sleeve is also provided. The method may include: providing at least one first generally flat sheet of a biologically-compatible material having at least one drug impregnated into the sheet; forming a plurality of apertures in the sheet; folding the sheet to form a rolled edge, an opposite free edge, a first open end, and a second open end opposite the first end; forming a seam along the free edge to close the free edge; and forming a seam along the second end to close the second end. The seam forming steps for the free edge and second end may be performed in any order. In another embodiment, the method may further include the step of laminating a second generally flat sheet of a biologically resorbable material having at least one drug impregnated onto the first sheet prior to forming the plurality of apertures and folding the sheets. In one embodiment, the biologically-compatible material is bioresorbable.

These foregoing and other features and advantages of the present invention will become apparent from the remainder of the disclosure, in particular the following detailed description of the preferred embodiments, all of which illustrate by way of example the principles of the invention.

DESCRIPTION OF THE DRAWINGS

The features of the preferred embodiments will be described with reference to the following drawings where like elements are labeled similarly, and in which:

FIG. 2 is a side cross-section view of the sleeve of FIG. 1;

FIG. 3 is a side cross-section view of an alternative embodiment of the sleeve of FIG. 1 containing multiple layers of a sheet or film;

FIG. 4 is a top view of the sleeve of FIG. 1 with the bone plate partially inserted into the sleeve;

FIG. 5 is a side view of an alternative embodiment of a drug-impregnated sleeve having an open-ended pocket formed on either end of the sleeve;

DETAILED DESCRIPTION OF THE PREFERRED EMBODIMENTS

In order that the invention may be understood, preferred embodiments which are given by way of example only, will now be described with reference to the appended drawings. Accordingly, the preferred embodiments are described for convenience of reference and without limitation of the invention to embodiments described herein. The scope of the invention being defined by the claims appended hereto.

Figure 1:
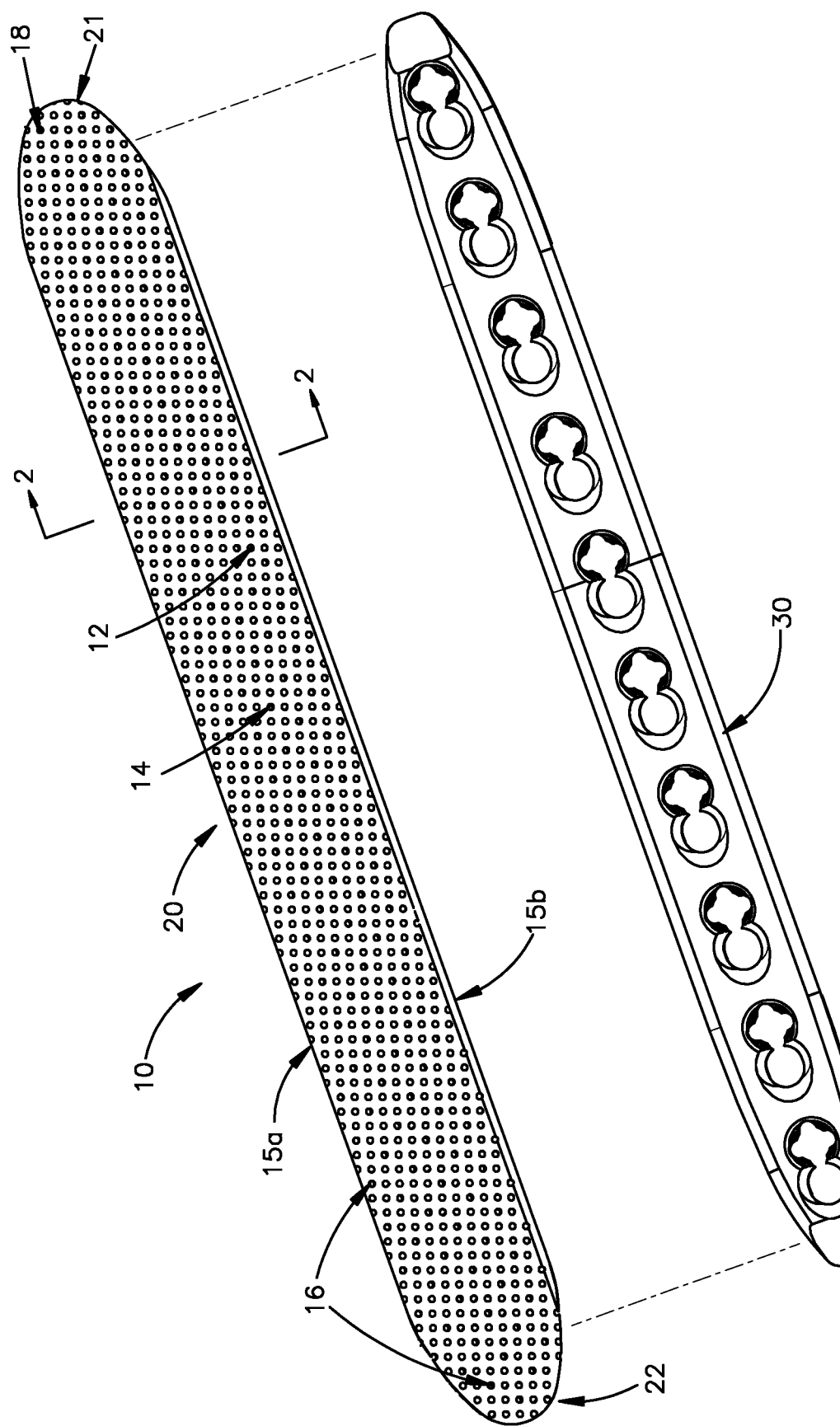
FIG. 1 is a top view of one embodiment of a drug-impregnated sleeve according to principles of the present invention and a medical implant in the form of a bone plate that is insertable into the sleeve.

FIG. 1 shows a drug-impregnated sleeve 10 according to principles of the present invention placed adjacent a medical device such as orthopedic implant 30, which in one non-limiting embodiment shown may be an elongate bone plate. FIG. 2 shows a cross-sectional view taken through sleeve 10 in FIG. 1.

Referring to FIGS. 1 and 2, a preferred embodiment of a drug-impregnated sleeve 10 may include an elongate body 20 having two ends 21, 22. Ends 21, 22 may be either opened or closed. In one embodiment, end 21 is preferably an open end through which an implant may be inserted into sleeve 10. Opposite end 22 preferably is closed end in one embodiment so that the implant may be snugly abutted against the closed end to achieve a better fit and prevent the sleeve from sliding in relation to the implant when the implant is affixed at the surgical site in the patient.

In one embodiment, sleeve 10 may be formed from a single thin sheet or film 12 of a biologically-compatible material. In a preferred embodiment, the biologically-compatible material is bioresorbable. Preferably, sheet 12 is generally flat prior to forming sleeve 10. Sheet 12 in a preferred embodiment is made of a biodegradable resorbable polymer which will dissolve away over time when implanted in vivo and be absorbed into a patient, leaving only the implant behind if the implant is not made of a resorbable material. Alternatively, the implant may also be made of a resorbable material in other embodiments in which case both the implant and sleeve will eventually dissolve. Sheet 12 may be generally thin and substantially planar in a preferred embodiment, which may without limitation have a typical illustrative thickness T in a range from about 0.02 mm to 0.5 mm, and more preferably in a range from about 0.04 mm to 0.1 mm. Any suitable sheet thickness T, however, may be used depending on the intended application, considerations for tear-resistance when inserting an implant into the sheet, drug dispensing duration, etc. Sheet 12 may be made by any suitable means known in the art.

In other embodiments, the drug delivery sleeve 10 may be formed by a textile process such as braiding, knitting, weaving, etc. In one embodiment, the textile sleeve may be fabricated using a fiber with the drug of interest impregnated into it. In one embodiment, the textile may also be formed from a bioresorbable fiber which does not contain a drug impregnated into the fiber. In that case, the textile material may then be coated with a layer of elastic bioresorbable polymer containing the drug of interest. In one embodiment, a textile implant may also be made in the form of a strip of elastic material, knitted woven, etc., with a bioresorbable adhesive coated on one or more sides, so that it can be adhered to the implant. In one embodiment, the drug of interest may be contained in the textile material, or in the adhesive component, or both.

In one embodiment of a flexible sleeve, the resorbable polymer used for sheet 12 preferably contains polycaprolocatone. Polymers containing at least a portion of resorbable, flexible polymers (e.g., a caprolactone) advantageously have properties of good flexibility and strength. In one embodiment, a flexible sleeve (e.g., made from polycaprolocatone) is readily stretchable to conform to the size and shape of the implant, but has sufficient strength to resist tearing during stretching the sleeve over the implant. In one preferred embodiment, sheet 12 containing caprolactone preferably is capable of stretching up to about 100% of its initial un-stretched length or width. Advantageously, a single stretchable sleeve may fit a wide range of implant sizes and/or shapes, and preferably provide a relatively snug fit over the medical implant in a preferred embodiment, with or without slight modification by the surgeon as described herein. In one embodiment, the present invention includes a kit including a limited number of sleeves of different sizes and/or shapes that may be able to fit over a majority of an implant product line.

In one embodiment of a resorbable flexible sleeve 10 having sufficient flexibility, sheet 12 may be composed of polycaprolactone and another resorbable polymer. A preferred illustrative non-limiting range for polycaprolactone content of the sleeve is from about 10% to about 100%, and more preferably from about 20% to 30%. In contrast to some other resorbable polymers typically used for implantation, polycaprolactone degrades relatively slowly in vivo. Accordingly, the caprolactone may be mixed with another polymer having quicker in vivo degradation times to control the overall degradation rate of sheet 12, while still retaining adequate flexibility for stretching sleeve 10 over a medical implant. In one possible embodiment, sheet 12 may be made of 30% polycaprolactone and 70% polylactic acid.

It will be appreciated that any other suitable percentages of polycaprolocatone may be used in sleeve 10. It will further be appreciated that other resorbable polymers or combinations of polymers may be used to make sheet 12, with or without polycaprolactone. For example, the polymer may be comprised of various combinations of any of the FDA approved monomers including glycolide, lactide, trimethylene carbonate, dioxanone and caprolactone. The film or fibers may also include synthetic polymers such as polyethylene oxide or bioresorbable polyurethane. In other embodiments, the film or fibers used to form the drug-impregnated sleeve may also include natural biopolymers such as gelatin, collagen, chitosan, hyaluronate, or alginates. Accordingly, the invention is not limited to the type of material, polymers, or combinations of polymers or other types of materials that used to make sheet 12.

In a preferred embodiment, sleeve 10 preferably further contains a plurality of apertures or perforations 14 of any suitable shape (such as substantially round perforations or apertures 14) in one possible embodiment to allow the passage or transport of fluids through the sleeve. Perforations 14 need not be perfectly round, and may be ovoid or elliptical in shape in some embodiments (not shown). The apertures 14 are not limited to round perforations 14. Preferably, perforations 14 extend completely through sheet 12 from an inside surface 11 to an outside surface 13 (see FIG. 2). Perforations 14 advantageously provide more even distribution of the drug or biological agent to adjacent tissue and bone as the material leaches out of the polymer than a sleeve without such perforations. In addition to benefiting drug distribution, perforations 14 also eliminates a dead space between the implant and sleeve where debris or material may become and remain trapped causing possible problems for the patient. Therefore, such debris may be flushed out and away through perforations 14 by bodily fluid flow.

A preferred illustrative non-limiting range for porosity based on percentage of open area provided by perforations 14 to total surface area of sheet 12 is from about 10% to about 80%, and more preferably from about 20% to about 50%. In one preferred embodiment, perforations 14 provide a porosity of about 20%. Perforations 14 preferably have a diameter of at least about 0.1 mm for satisfactory drug distribution and flushing. In a preferred embodiment, perforations 14 have a diameter of at least about 1.5 mm. Diameters of approximately 0.1 mm or greater are generally considered in the art to represent macroporosity.

Preferably, in one embodiment, perforations 14 are made while sheet 12 is in a generally flat state before being formed into sleeve 10, as further described herein.

Sleeve 10 may be made in one embodiment using a thermally processed, compression molded sheet of degradable polymer. In one embodiment, the drug or other biological agent may be dissolved or dispersed into the polymer while still in solution form. In one embodiment, the polymer solution is then processed into a sheet or film using conventional methods known in the art, perforated, and then fashioned into a sleeve as described herein. Preferably, sheet 12 may be perforated by any suitable technique, such as using a press in one embodiment, while the sheet is still in a generally flat state.

In one embodiment, sleeve 10 may be formed from perforated sheet 12 by folding the sheet over itself to create a longitudinally-extending free edge 15a and a longitudinally-extending rolled or folded edge 15b, as shown in FIGS. 1 and 2. Free edge 15a and ends 21, 22 thus initially may have a double layer or thickness T of sheet 12 where the sheet overlaps itself (see FIG. 2). Rolled edge 15b may have a generally slightly rounded, curved shape or a crease in transverse cross-section comprising a single layer or thickness T of sheet 12 (see also FIG. 2). The sheet forming edge 15*a* and preferably end 22 may then be joined together (e.g., by heat fusion welding) in one embodiment to create a fused seam 16 along edge 15*a* and end 22. In one embodiment, sleeve 12 thus formed defines an internal cavity 23 configured for receiving an implant. Preferably, in one embodiment, end 21 is not joined together to define and create opening 18 in end 21 for inserting the implant into sleeve 10. It should be noted that any suitable technique may be used to form a seal and close free edge 15*a* and end 22, such as chemical fusion or welding, use of biologically compatible adhesives, etc. Accordingly, the invention is not limited to the use of heat fusion techniques.

In other embodiments, sleeve may be formed by methods other than folding and seaming a flat sheet of a biocompatible material. In one embodiment shown in FIG. 10, a sleeve 100 may be formed in the shape of a tube 112 having apertures or perforations 114 and two ends 116, 118. Preferably, in one embodiment, tube 112 is seamless, hi one possible embodiment, tube 100 may be made of polymer. A polymeric tube 112 may be formed in some possible embodiments by pour-casting or dip-molding processes. The pour-casting method preferably includes pouring a polymer solution into a tubular-shaped mold, allowing the polymer to solidify, and removing the formed tubular sleeve 112 from the mold. The dip-molding process preferably includes in one embodiment dipping a rod-like mandrel into a container of polymer solution, withdrawing the mandrel from the solution with the polymer clinging to the mandrel, solidifying the polymer, and removing the formed tubular sleeve 112 from the mandrel. The polymer solution used in the dipping process preferably has a suitable viscosity to allow the polymer to adhere to the mandrel. A dip-molding process that may be used in forming sleeve 112 is disclosed in U.S. Patent Application Publication No. 20050209629, which is incorporated herein by reference in its entirety. In some embodiments, the mandrel may be dipped more than once to increase the thickness of the tubular sleeve 112. In other embodiments, the mandrel may be dipped into two or more containers of the same or different types of polymer solutions to create a multi-layered tube 112. In some embodiments, the two or more of the same or different polymer solutions may include the same drug, different salts of the same drug, different drugs, or any combination thereof. Accordingly, tubular sleeve 112 may be made with multiple polymer layers that allow the type of drug dispensed and the dispending rate and duration to be controlled as required for a particular application.

Figure 10:
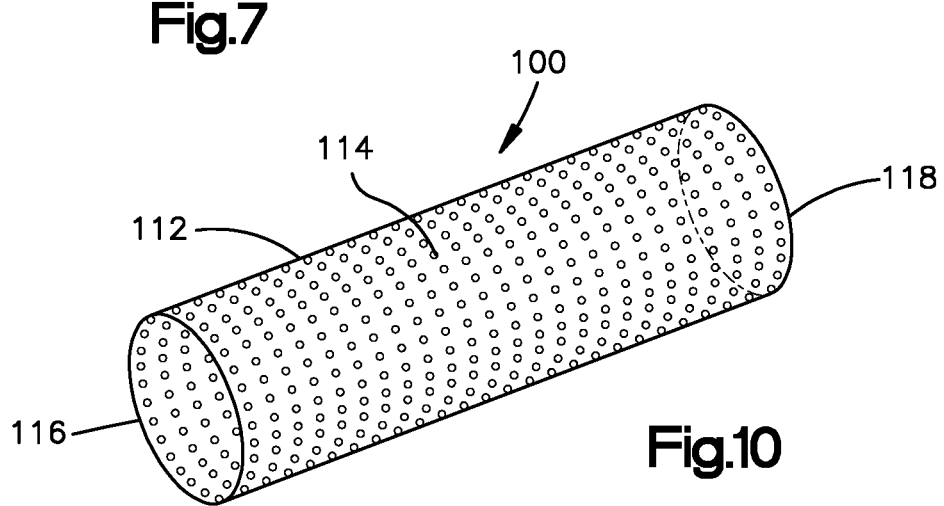
FIG. 10 is a perspective view of an alternative tubular drug-impregnated sleeve.

Apertures or perforations 114 may be formed in tube 112 by any suitable means. In one embodiment, tube 112 may be flattened after it solidifies if the tube material selected has sufficient elasticity. Perforations 114 can then be made by any suitable means, such as without limitation using a press or other device to pierce/puncture the flattened tube. If tube 112 is made of an inelastic material in some embodiments that cannot be readily flattened, perforations 114 may be created by any suitable means to puncture the tube and create the perforations. In another possible embodiment used in conjunction with casting molding tube 112, the mold may be provided with a plurality of posts or pins sized and configured to match the intended final shape and size of perforations 114. As the polymer solution is poured into the mold, the solution will flow around the posts or pins. Perforations 114 will form as the polymer solidifies at the same time that the tubular sleeve is made. Cast-forming perforations 114 in the foregoing manner avoids an additional manufacturing step for making the perforations after tube 112 is made. Tube 112 may be made with either open ends 116, 118 as shown in FIG. 10, or in some embodiments either end 116, or 118 may be formed as a closed end (not shown). A sleeve 10 made in the form of a seamless tube may generally have better strength than a folded and seamed sleeve in some embodiments.

As shown in FIG. 2, before inserting a medical implant into sleeve 10, one embodiment of the sleeve may have a generally flattened oval or elliptical shape in a transverse cross section to the length of the sleeve defined as extending in the direction of edge 15*a*. Accordingly, the top 17*t* and bottom 17*b* of sleeve 10 may include generally planar or flat portions which in one possible embodiment will generally conform to the shape of complementary flat implants 30 as shown to eliminate unnecessary excess loose sleeve material (after the implant is inserted) that may form undesirable excessively large pockets between the sleeve and implant wherein debris may become entrapped in vivo. In other embodiments (not shown), sheet 12 may be folded and sleeve 10 formed so that almost a tubular shape may be created.

It is important to note that the polymer constituents can be varied to create a wide range of resorbtion profiles. In addition, alternative film production methods can be employed, particularly if the drug of interest is thermally degraded at the temperatures employed in the compression molding process. Lower temperature film production methods such as but not limited to solvent casting and dip molding on mandrels may alternatively be used.

Sleeve 10 preferably is supplied separately in its own sterile pouch. The surgeon may use sleeve 10 by removing the sleeve from the pouch, and then sliding and stretching the sleeve over an implant 30. Implant 30 may be slid into sleeve 10 all the way into or close to closed end 22 to achieve a relatively snug fit and avoid excessive unsupported loose sleeve material on the end. Sleeve 10 may further be trimmed using a surgical scissors to remove excess sleeve length by cutting end 21 off close to the end of the implant 30. It should be noted that although a somewhat snug fit between sleeve 10 and implant 30 may be desired in some circumstances to avoid excessively loose material that might interfere with installing implant 30 at the surgical site; a tight fit is not required in all instances. Similar techniques described above may be used by the surgeon to modify sleeve 10 for custom fitting the sleeve to the particular size and shape of the implant needed to be encased. The implant encased within the sleeve may then be implanted into the patient and fixed in place using standard methods. Advantageously, the surgeon will be able to deploy a drug from a variety of implants via the sleeve, but medical device companies will avoid the onerous logistics of developing and maintaining large uncoated and coated implant inventories, with one or more drugs depending on the condition of the patient or indication to be treated.

Although medical implant 30 is shown as being a straight elongate plate, it will be appreciated that numerous different shapes and types of medical implants may be used with the invention without limitation. Accordingly, sleeve 10 may be used with devices other than bone plates, such as without limitation non-orthopedic implants (e.g., stents, pacemakers, dental implants, etc.) and other orthopedic implants (e.g., tibia nails, femoral nails, spinal implants, etc.). Accordingly, in some embodiments, the surgeon may combine two or more sleeves 10 of the same or different sizes and shapes for an implant with a more complex shape. For example, two or more sleeves 10 may be combined without limitation for use with bone plates or other types of medical implants having an L-shape, T-shape, X-shape, H-shape or other types and shapes of implants. It should be recognized that the implant need not be completely encased by sleeve 10 in all cases to effectively deliver a drug or other biological agent to surrounding tissue. Therefore, a variety of implant shapes may be accommodated by using a combination of sleeves 10.

With reference to FIG. 5, an alternative embodiment of a sleeve 40 is shown that is designed so that the drug is released from only one side of the implant to direct the drug into bone or the nearby soft tissue as desired. This sleeve 40 embodiment includes an open center portion 42 with only a single thickness of sheet 12 and a pocket 44 formed on either end portion 46. This open configuration leaves one side of implant 30 exposed between pockets 44 and may be supplied to the surgeon in the form shown or created by the surgeon in the operating room by cutting the center part out of sleeve 10 (shown in FIG. 1).

In another possible embodiment, sleeve 10 may be placed over autograft or allograft bone prior to implantation for drug dispensing and/or to use the sleeve as a bone graft containment device. For example, bone marrow aspirate (BMA) is often mixed with a carrier such as ChronOS granules (available from Synthes, Inc. of West Chester, Pa.) or other forms. In one embodiment, the surgeon may fill the sleeve with the ChronOS-BMA mixture to prevent migration of the mixture away from the implant site. Some examples of other suitable carrier material include a calcium phosphate cancellous bone substitutes such as Vitoss® (r) (available from Orthovita of Malvern, Pa.), or Conduit™ (r) (available, from DePuy, Inc. of Raynham, Mass.).

In one embodiment, the resorbtion time of the polymer sleeve and concomitant drug dispensing rates can be manipulated from days to years. The polymer chemistry and type of polymer used provide a wide range of possible drug delivery kinetics and polymer resorbtion times. In addition, resorbtion times and drug delivery rates can be manipulated by the thickness of sheets used to construct the polymer sleeve.

Other techniques may be employed for controlling the delivery rate and duration of delivery for drugs or biological agents from the sleeve. For example, in one alternative embodiment shown in FIG. 3, sleeve 50 may be formed from multiple layers of polymer sheets having the same or different compositions of polymers. Sleeve 50 may include two sheets 12 and 52 which in one embodiment, have been laminated together, by any conventional method known in the art, and may include perforations 50 as shown. In some embodiments, both sheets 12 and 52 need not each contain perforations 14 if not desirable. In one embodiment, a drug may be impregnated into each sheet 12, 52, but the sleeve may be designed to release the drug at different rates. In one embodiment, this may be accomplished by making one or more sheets 12, 52 microporous, to allow more rapid water or fluid penetration into the film, and more rapid elution of the drug. Non-microporous layers would entrap the drug more effectively, causing it to elute at a slower rate. In other embodiments having sheets 12 and 52 made from different polymers, one sheet could be more hydrophillic and swell at a faster rate by fluid absorption than the other sheet, thereby releasing the drug more rapidly. Alternatively, one of the sheets 12 or 52 may be made from a polymer that degrades in vivo more quickly than the other sheet. In some embodiments, the same drug or biological agent may be incorporated in sheets 12 and 52. In other embodiments, a different drug may be contained in sheets 12 and 52. Accordingly, for example, a first type of drug may be delivered from sheet 12 at a given rate and duration while a second different or the same drug may be delivered form sheet 52 at a given rate and duration which may be different.

In other embodiments, a drug or biological agent may be delivered at different rates and durations by incorporating different salts of one or more types of drug into sleeve 10 or 50. In one embodiment, sheet 12 of sleeve 10 may contain different salts of the same drug, each of which will have different solubilities in body fluid. Therefore, the drug release rate will vary according to the solubility of the particular salt. In one embodiment, this would allow the elution profile of the drug from the sheet 12 to be controlled by changing the ratios of different salts of the same drug present in the sheet. In another embodiment, sheet 12 may contain different salts of two or more different drugs or biological agents. In alternative embodiments of a sleeve 50 having multiple layers of sheets 12, 52, sheet 12 may contain a different salt of the same drug than sheet 52.

Figure 6:
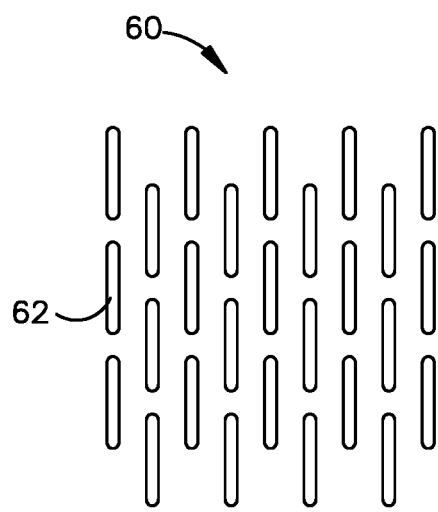
FIG. 6 is a top view of an alternative embodiment of a drug-impregnated sleeve having deformable apertures in the form of slots.
Figure 8:
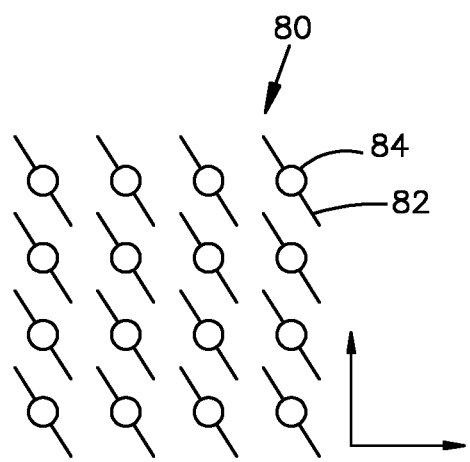
FIG. 8 is a top view of an alternative embodiment of a drug-impregnated sleeve having deformable apertures in the form of slits and holes.
Figure 7:
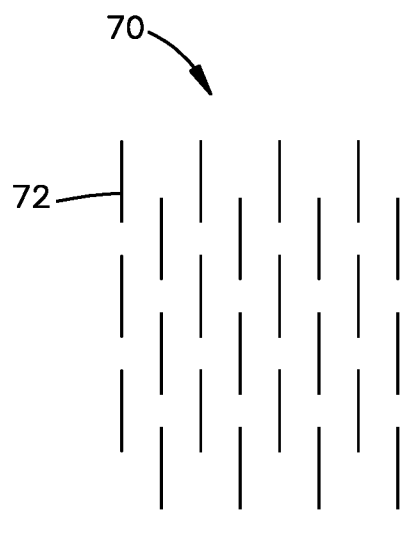
FIG. 7 is a top view of an alternative embodiment of a drug-impregnated sleeve having deformable apertures in the form of slits.
Figure 9:
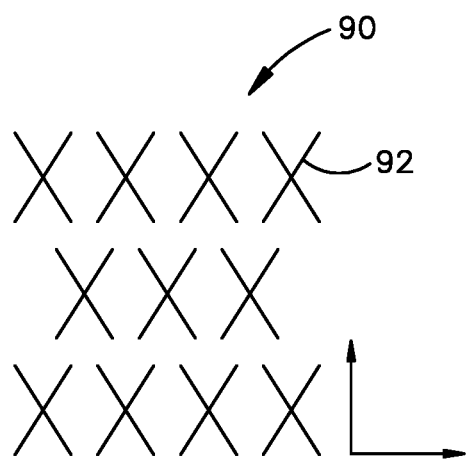
FIG. 9 is a top view of an alternative embodiment of a drug-impregnated sleeve having deformable apertures in the form of x-shaped slits.

Referring to FIGS. 6-9, alternative embodiments of sleeves 10 or 50 may be produced from a polymer sheet or film which is not completely flexible or elastic to allow expansion or stretching over an implant, but may be made to expand to fit a number of different size implants by providing a pattern of deformable apertures such as holes and/or slits/slots cut into the sleeves at various orientations. The holes and/or slits/slots would deform, and allow the sleeve to stretch over the implant. FIG. 6 shows one possible embodiment of a polymer sheet 60 including longitudinally-extending slots 62. This arrangement allows sheet 60 to stretch across its width (running horizontally) in the direction of the stretch arrows shown. FIG. 7 shows one possible embodiment of a polymer sheet 70 including longitudinally-extending slits 72. This arrangement allows sheet 70 to stretch across its width (running horizontally) in the direction of the stretch arrows shown. FIG. 8 shows one possible embodiment of a polymer sheet 80 including a combination of longitudinal slits 82 and holes 84 with the slits being oriented diagonally on the sheet in the embodiment shown. This arrangement allows sheet 80 to stretch across its width (running horizontally) and length (running vertically) in the direction of the stretch arrows shown. FIG. 9 shows one possible embodiment of a polymer sheet 90 including X-shaped slits 92. This arrangement allows sheet 90 to stretch across its width (running horizontally) and length (running vertically) in the direction of the stretch arrows shown. In alternative embodiments of sheet 90, X-shaped slots may be provided in lieu of slits.

It will be appreciated that various other suitable shapes, combinations, and patterns of deformable apertures such as holes, slits, and slots may be used so long as the polymer sheet is capable of being expanded or stretched in one or more directions. It should be recognized that the deformable apertures may be used with flexible, semi-rigid, or rigid sheets of polymer where a highly stretchable sleeve is desired. The deformable apertures may advantageous be used for encasing irregularly shaped implants which are not totally linear in profile.

While the description and drawings represent preferred embodiments of the present invention, it will be understood that various additions, modifications and substitutions may be made therein without departing from the spirit and scope of the present invention as defined in the accompanying claims, hi particular, it will be clear to those skilled in the art that the present invention may be embodied in other specific forms, structures, arrangements, proportions, sizes, and with other elements, materials, and components, without departing from the spirit or essential characteristics thereof. One skilled in the art will appreciate that the invention may be used with many modifications of structure, arrangement, proportions, sizes, materials, and components used in the practice of the invention, which are particularly adapted to specific needs and operating requirements, without departing from the principles of the present invention. The presently disclosed embodiments are therefore to be considered in all respects as illustrative and not restrictive, the scope of the invention being defined by the appended claims, and not limited to the foregoing description or embodiments.

What is claimed is:

1. A bone graft containment system comprising:
a biocompatible sleeve comprising a textile body made of one or more polymer fibers, the sleeve including
a top and a bottom,
a first end open for receiving a bone graft material, and
a second end, the second end including a seam closing the second end,
the sleeve defining an internal cavity configured to contain the bone graft material,
and a bone graft material disposed within the cavity.

2. The bone graft containment system according to claim 1, wherein the sleeve comprises a biocompatible sheet.

3. The bone graft containment system according to claim 2, wherein the sheet has a thickness in the range of about 0.02 mm to about 0.5 mm.

4. The bone graft containment system according to claim 2, wherein the sheet has a thickness in the range of about 0.04 mm to about 0.1 mm.

5. The bone graft containment system according to claim 1, wherein the textile body further comprises a bioresorbable coating layer on the one or more polymer fibers.

6. The bone graft containment system according to claim 1, wherein the sleeve comprises a resorbable polymer or a mixture of resorbable polymers.

7. The bone graft containment system according to claim 1, wherein the sleeve further comprises a first edge, the first edge having a seam closing the first edge.

8. The bone graft containment system according to claim 1, wherein the bone graft material comprises bone marrow aspirate.

9. The bone graft containment system according to claim 1, wherein the bone graft material comprises autograft material.

10. The bone graft containment system according to claim 1, wherein the bone graft material comprises allograft material.

11. The bone graft containment system according to claim 1, wherein the bone graft material comprises calcium phosphate bone substitute material.

12. The bone graft containment system according to claim 1, wherein the sleeve further includes one or more drugs impregnated in the sleeve.

13. The bone graft containment system according to claim 12, wherein the one or more drugs includes an antibiotic, antiseptic, analgesic, antineoplastic agent, bisphosphonate, growth factor, peptide, statin, or combination thereof.

* * * * *